United States Patent [19]
Guzek et al.

[11] Patent Number: 5,763,626
[45] Date of Patent: Jun. 9, 1998

[54] MALTOL RECOVERY

[75] Inventors: Donald B. Guzek, Stonington, Conn.; Kenneth D. Dickey, Westerly, R.I.; Russell J. Hausman, East Lyme, Conn.

[73] Assignee: Cultor Ltd., Helsinki, Finland

[21] Appl. No.: 732,337

[22] PCT Filed: Apr. 3, 1995

[86] PCT No.: PCT/IB95/00224

§ 371 Date: Oct. 28, 1996

§ 102(e) Date: Oct. 28, 1996

[87] PCT Pub. No.: WO95/29908

PCT Pub. Date: Nov. 9, 1995

[51] Int. Cl.[6] .................................................. C07D 315/00
[52] U.S. Cl. .................................................. 549/418
[58] Field of Search .................................................. 549/418

[56] References Cited

U.S. PATENT DOCUMENTS

| | | | |
|---|---|---|---|
| 3,501,501 | 3/1970 | Heintz et al. | 260/345.9 |
| 4,082,717 | 4/1978 | Brennan et al. | 260/345.9 |
| 4,342,697 | 8/1982 | Weeks et al. | 549/396 |
| 5,221,756 | 6/1993 | Fleisher et al. | 549/418 |

FOREIGN PATENT DOCUMENTS 5 505 7 582  4/1980  Japan.

OTHER PUBLICATIONS

Pavia, et al., Intro. to Org. Lab. Tech., Saunders, 1976, pp. 525–528.

Takaishi, K., Phytochemistry 10:3302 (1971).

*Primary Examiner*—Amelia Owens
*Attorney, Agent, or Firm*—St. Onge Steward Johnston & Reens LLC

[57] ABSTRACT

Pure maltol is recovered from a mixture containing maltol by extraction into an aqueous solution, optionally in the presence of a substantially water-immiscible solvent in which the maltol in the mixture is substantially insoluble.

17 Claims, No Drawings

MALTOL RECOVERY

The present invention is directed to a process for obtaining maltol and more particularly to a process for obtaining pure maltol.

Maltol (3-hydroxy-2-methyl-4H-pyran-4-one) is a heterocyclic aroma chemical used extensively in flavor, fragrance and in some pharmaceutical compositions. Maltol occurs naturally in numerous plant species and its isolation from these sources has been reported extensively in the literature. In particular, its isolation from coniferous trees such as larch trees (*Larix decidua* mill), pine trees and pine needles (*Abis alba* mill., pinaceae), has been reported since the turn of the century.

U.S. Pat. No. 5,221,756 issued Jun. 22, 1993 refers to a process for the recovery of maltol from a mixture of maltol by co-distillation with an aliphatic or cycloaliphatic hydrocarbon in which the maltol is substantially insoluble; and then condensing the co-distillate to recover substantially pure crystals of maltol.

Maltol has been obtained from the destructive distillation of wood but such process only results in small amounts of maltol. Thus, such a process is economically undesirable.

Fleisher & Fleisher, "Water-soluble Fractions of the Essential Oils", Perfumer and Flavorist, Vol. 16 May/June, pp. 37–41, 1991, refers to the recovery and characterization of compounds from fir needles (*Abis balsamea* L.).

U.S. Pat. Nos. 3,031,204, 4,082,717 and 4,343,697 refer to processes for the synthesis of gamma pyrones, such as maltol, ethyl maltol and pyromeconic acid.

The present invention is directed to a process for the recovery of maltol comprising:

a) heating a mixture containing maltol in the presence of a substantially water-immiscible solvent in which the maltol in said mixture is substantially insoluble to form an aqueous layer and a solvent layer; and b) recovering said aqueous layer.

Further preferred is the process wherein maltol is recovered from the aqueous layer.

Preferred is the process wherein said solvent is selected from the group consisting of hexane, α-pinene and petroleum ether; and combinations thereof.

Also preferred is the process wherein said solvent is hexane.

Also preferred is the process wherein said solvent is α-pinene.

Also preferred is the process wherein said solvent is petroleum ether.

Especially preferred is the process wherein said mixture is a resin.

Also preferred is the process wherein said resin is derived from solvent extraction of a coniferous species with a preferred coniferous source being needles with especially preferred needles being derived from *Abis balsamea* L fir trees.

Also preferred is the process wherein the solubility of maltol in said solvent is less than about 0.3% percent by weight at room temperature.

The present invention is also directed to substantially pure maltol produced by the process of the present invention.

In a further embodiment, the present invention is directed to a process for the recovery of maltol comprising (a) heating an oleoresin containing maltol in the presence of an aqueous solution to create an aqueous layer and a resin layer;

(b) recovering said aqueous layer.

Further preferred is the process wherein maltol is recovered from the aqueous layer.

Especially preferred is the process wherein the oleoresin is derived from solvent extraction of coniferous species with an especially preferred coniferous source being needles with especially preferred needles being derived from *Abis balsamea* L fir trees.

Also preferred is the process wherein the aqueous solution is added at a weight of from about 0.5 to about 5 times the weight of the oleoresin.

The present invention is directed to a process for the recovery of pure maltol from a mixture containing maltol. The mixture may be any mixture derived from, for example, plant species or coniferous trees known to contain maltol. Preferably, the mixture is a resin derived from extraction of pine tree needles, or larch tree bark, both sources high in natural maltols. Preferably, the mixture is derived from extraction of needles derived from the fir tree (*Abis balsamea* L.). The crude resin derived from, for example, fir trees, normally contains 3 to 8% maltol.

If, for example, a fir tree resin is used, the codistillation process referred to in U.S. Pat. No. 5,221,756 requires large quantities of the hydrocarbon solvent in both the codistillation and condensation step.

In the present invention, it has been found that the resin, for example, can be heated in the presence of a solvent in which the maltol is substantially insoluble. The temperature of the heating step can range from about 35° C. to about 100° C.

Preferably, the solubility of maltol in the solvent is less than about 0.3% by weight at room temperature. Suitable solvents are any solvent in which maltol is substantially insoluble. Preferred solvents are organic solvents such as hexane, α-pinene and, petroleum ether. Especially preferred solvents are hexane and α-pinene. The amount of solvent used may vary depending on the material from which the maltol is being extracted. If, for example, the maltol is being extracted from a fir needle resin, the weight of solvent would be approximately equal to the weight of the resin.

In the process of the present invention, an aqueous solution is added to the aforementioned solvent/maltol mixture product. The term aqueous solution encompasses water as well as any other solution containing substantial quantities of water. The amount of aqueous solution used can also vary depending on the material from which the maltol is being extracted. If, for example, the maltol is being extracted from a fir tree needle resin, the weight of aqueous solution would be approximately equal to the weight of the previously formed solvent/maltol mixture composition. Heating of this product results in a composition with two liquid phases wherein the aqueous phase contains maltol.

If desired, maltol may be extracted in a series of steps by removal of the aqueous layer followed by addition of an aqueous solution to the remaining resin, for example, to create another aqueous layer from which the maltol may be recovered.

Moreover, if the starting mixture of maltol is an oleoresin derived from, for example, solvent extraction of fir tree needles, the maltol may be extracted by heating, for example, to about 80° C., the oleoresin in the presence of an aqueous solution.

Having described the invention in general terms, reference is now made to specific examples. It is to be understood that these examples are not meant to limit the present invention, the scope of which is determined by the appended claims.

EXAMPLE 1

Extraction of Maltol in Presence of Hexane Cosolvent

Fir balsam oleoresin derived from the solvent extraction of *Abis balsamea* L. needles was mixed with an equal weight of hexane and the mixture was heated with agitation until uniform. A weight of water equal to the weight of the resin-hexane mixture was added and the mixture was stirred vigorously at hexane reflux temperature (69° C.) for 45 minutes. The mixture was transferred to a separation funnel equipped with a condenser and steam jacket, reheated to hexane reflux temperature, and allowed to separate. The aqueous layer was collected, weighed and assayed for maltol.

A second weight of water equal to the initial weight was added to the hexane-resin mixture and the extraction procedure was repeated.

|  | First extraction | Second extraction |
| --- | --- | --- |
| Weight of aqueous layer, grams | 193 | 194 |
| Concentration of maltol in aqueous layer, percent | 1.46 | 0.59 |
| Percentage of maltol extracted into aqueous layer | 57.2 | 23.3 |

The combined maltol yield for the two extractions was 80.5%.

EXAMPLE 2

Extraction of Maltol in Presence of α-Pinene Cosolvent

Fir balsam oleoresin derived from the solvent extraction of *Abis balsamea* L. needles was mixed with an equal weight of α-pinene and the mixture was heated with agitation until uniform. A weight of water equal to the weight of the resin-pinene mixture was added and the mixture was stirred vigorously at 70°–80° C. for 45 minutes. The mixture was transferred to a separation funnel equipped with a condenser and steam jacket, reheated, and allowed to separate. The aqueous layer was collected, weighed and assayed for maltol.

A second weight of water equal to the initial weight was added to the pinene-resin mixture and the extraction procedure was repeated.

|  | First extraction | Second extraction |
| --- | --- | --- |
| Weight of aqueous layer, grams | 155 | 187 |
| Concentration of maltol in aqueous layer, percent | 1.56 | 0.75 |
| Percentage of maltol extracted into aqueous layer | 49.8 | 28.9 |

The combined maltol yield for the two extractions was 78.7%.

EXAMPLE 3

Degree of Phase Separation for Various Solvents

Fir balsam oleoresin obtained by solvent extraction of *Abis balsamea* L. needles was mixed with an equal weight of solvent, and the mixture was heated and stirred to form a uniform mixture. A weight of water equal to the weight of the resin-solvent mixture was added and the mixture was stirred vigorously with heating, then allowed to separate. The following observations were made on degree of separation:

| Solvent | Separation |
| --- | --- |
| Hexane | Good |
| Toluene | Poor |
| Petroleum ether | Good |
| α-pinene | Good |

EXAMPLE 4

Maltol Solubility in Various Solvents

Maltol solubility at room temperature in the solvents of Example 2 was determined by filtering saturated solutions and assaying the filtrates.

| Solvent | Maltol concentration, percent |
| --- | --- |
| Hexane | 0.043 |
| Toluene | 0.46 |
| Petroleum ether | 0.05 |
| α-pinene | 0.12 |

EXAMPLE 5

Partitioning of Maltol in Water-Solvent Systems

Mixtures of one part solvent, one part resin, and two parts water were stirred vigorously for 5 minutes at about 40° C., then allowed to separate. The aqueous layers were assayed for maltol.

| Solvent | Concentration of maltol in aqueous layer, percent |
| --- | --- |
| Hexane | 1.62 |
| Toluene | 1.15 |
| Petroleum ether | 1.24 |
| α-pinene | 1.60 |

Based on these data, hexane and α-pinene are preferred cosolvents for extraction of maltol into aqueous solution.

EXAMPLE 6

Aqueous Extraction of Maltol Without a Cosolvent

Fir balsam oleoresin derived from the solvent extraction of *Abis balsamea* L. needles was mixed with an equal weight of water and the mixture was heated to 80° C. with agitation for one hour. Agitation was discontinued and the mixture was held at 80° C. for 45 minutes to allow phase separation. The mixture was cooled to 55° C. and the aqueous and resin layers were isolated. The following data were obtained:

| | |
| --- | --- |
| Weight of aqueous layer | 90.0 grams |
| Weight of resin layer | 99.3 grams |
| Concentration of maltol in aqueous layer | 2.2% |
| Concentration of maltol in resin layer | 2.68% |

| | |
|---|---|
| Portion of maltol extracted into aqueous layer | 42.8% |
| Portion of maltol extracted into resin layer | 57.2% |

EXAMPLE 7

Aqueous Extraction of Maltol Without a Cosolvent

Fir balsam oleoresin derived from the solvent extraction of *Abis balsamea* L. needles was mixed with 1.5 times its weight of water and the mixture was heated to 80°–85° C. with agitation for one hour. Agitation was discontinued and the mixture was held at 80°–85° C. for 45 minutes to allow phase separation. The aqueous layer was isolated, weighed, and assayed for maltol.

| | |
|---|---|
| Weight of aqueous layer | 127.5 grams |
| Concentration of maltol in aqueous layer | 1.84% |
| Portion of maltol extracted into aqueous layer | 59.5% |

We claim:

1. A process for the recovery of maltol comprising:
   a) heating a mixture containing maltol with an aqueous solution and a substantially water immiscible solvent in which the maltol in said mixture is substantially insoluble to form an aqueous layer containing maltol and a solvent layer;
   b) allowing the aqueous layer to separate from the solvent layer to form two liquid phases; and
   c) recovering said aqueous layer to obtain maltol extracted from the mixture.

2. The process of claim 1 further comprising the step of recovering maltol from the aqueous layer.

3. The process of claim 1 wherein said solvent is selected from the group consisting of hexane, α-pinene and petroleum ether; and combinations thereof.

4. The process of claim 3 wherein said solvent is hexane.

5. The process of claim 3 wherein said solvent is α-pinene.

6. The process of claim 3 wherein said solvent is petroleum ether.

7. The process of claim 1 wherein said mixture is a resin.

8. The process of claim 7 wherein said resin is derived from solvent extraction of needles from coniferous species.

9. The process of claim 8 wherein said needles are from *Abis balsamea* L fir trees.

10. The process of claim 1 wherein the solubility of maltol in said solvent is less than about 0.3% percent by weight at room temperature.

11. Substantially pure maltol produced by the process of claim 1.

12. A process for the recovery of maltol comprising
    (a) heating an oleoresin containing maltol in the presence of an aqueous solution to create an aqueous layer containing maltol and a resin layer;
    (b) allowing the layers to separate into two liquid phases; and
    (c) recovering said aqueous layer to obtain maltol extracted into the aqueous solution.

13. The process of claim 12 further comprising the step of recovering maltol from the aqueous layer.

14. The process of claim 12 wherein the oleoresin is derived from solvent extraction of needles of coniferous species.

15. The process of claim 14 wherein said needles are from *Abis balsamea* L. fir trees.

16. The process of claim 12 wherein the aqueous solution is added at a weight of from about 0.5 to about 5 times the weight of the oleoresin.

17. Substantially pure maltol produced by the process of claim 12.

* * * * *